United States Patent
MacLoughlin et al.

(10) Patent No.: US 11,833,310 B2
(45) Date of Patent: Dec. 5, 2023

(54) HIGH FLOW NASAL THERAPY SYSTEM

(71) Applicant: Stamford Devices Limited, Galway (IE)

(72) Inventors: Ronan MacLoughlin, Galway (IE); Niall Smith, Central Scotland (GB)

(73) Assignee: Stamford Devices Limited, Galway (IE)

( * ) Notice: Subject to any disclaimer, the term of this patent is extended or adjusted under 35 U.S.C. 154(b) by 988 days.

(21) Appl. No.: 16/750,507

(22) Filed: Jan. 23, 2020

(65) Prior Publication Data

US 2020/0155788 A1    May 21, 2020

Related U.S. Application Data

(63) Continuation of application No. 15/301,318, filed as application No. PCT/EP2015/057866 on Apr. 10, 2015, now Pat. No. 10,617,840.

(30) Foreign Application Priority Data

Apr. 11, 2014  (EP) ..................................... 14164468

(51) Int. Cl.
  *A61M 16/08* (2006.01)
  *A61M 16/06* (2006.01)
  (Continued)

(52) U.S. Cl.
  CPC ............ *A61M 16/16* (2013.01); *A61M 11/00* (2013.01); *A61M 15/08* (2013.01);
  (Continued)

(58) Field of Classification Search
  CPC ...... A61M 11/00; A61M 11/02; A61M 11/06; A61M 15/0016; A61M 15/0086;
  (Continued)

(56) References Cited

U.S. PATENT DOCUMENTS 4,686,974 A * 8/1987 Sato .................... A61M 16/024
                                                                    128/207.18
4,747,403 A    5/1988 Gluck et al.
(Continued)

FOREIGN PATENT DOCUMENTS

DE    10 2010 054361 A1    6/2012
FR         2783431 A1    3/2000
(Continued)

OTHER PUBLICATIONS

International Search Report and Written Opinion in corresponding International Application No. PCT/EP2015/057866 dated Jun. 12, 2015 (12 pages).

*Primary Examiner* — Annette Dixon
(74) *Attorney, Agent, or Firm* — Bookoff McAndrews, PLLC

(57) ABSTRACT

A high flow nasal therapy system (1) has a gas supply (2), a nebulizer (12), and a nasal interface (7). There are two branches (11, 10) and a valve (6) linked with the controller, the branches including a first branch (11) for delivery of aerosol and a second branch (10) for delivery of non-aerosolized gas. The controller controls delivery into the branches (11, 10), in which flow is unidirectional in the first and second branches, from the gas supply towards the nasal interface. The first branch (11) includes the nebulizer (12) and a line configured to store a bolus of aerosol during flow through the second branch (10). The valve (6) comprises a Y-junction between the gas inlet on one side and the branches on the other side.

20 Claims, 6 Drawing Sheets

Figure 1:
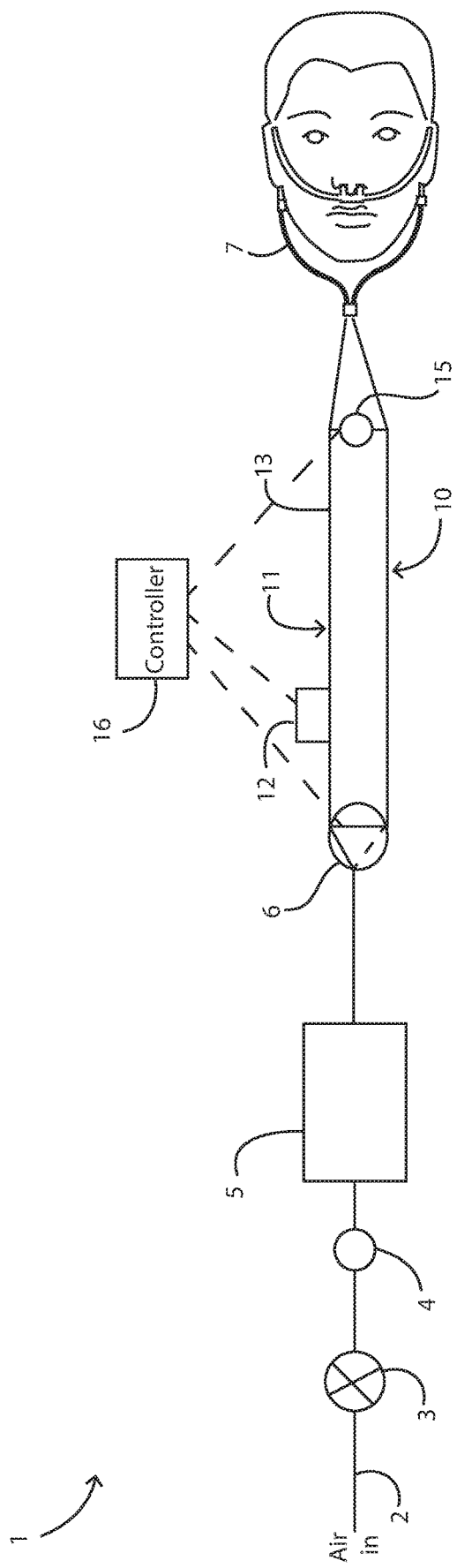

(51) Int. Cl.
| | | |
|---|---|---|
| *A61M 16/16* | (2006.01) | |
| *A61M 16/20* | (2006.01) | |
| *A61M 11/00* | (2006.01) | |
| *A61M 15/08* | (2006.01) | |
| *A61M 16/14* | (2006.01) | |
| *A61M 16/10* | (2006.01) | |
| *A61M 16/00* | (2006.01) | |

(52) U.S. Cl.
CPC .... *A61M 16/0666* (2013.01); *A61M 16/0833* (2014.02); *A61M 16/0866* (2014.02); *A61M 16/0875* (2013.01); *A61M 16/1095* (2014.02); *A61M 16/14* (2013.01); *A61M 16/202* (2014.02); *A61M 2016/0018* (2013.01); *A61M 2016/0027* (2013.01); *A61M 2016/0033* (2013.01); *A61M 2016/0036* (2013.01); *A61M 2205/33* (2013.01); *A61M 2205/3334* (2013.01)

(58) Field of Classification Search
CPC .............. A61M 15/08; A61M 16/0051; A61M 16/0066; A61M 16/0069; A61M 16/024; A61M 16/06; A61M 16/0666; A61M 16/0677; A61M 16/0688; A61M 16/08; A61M 16/0825; A61M 16/0833; A61M 16/0866; A61M 16/0875; A61M 16/101; A61M 16/1055; A61M 16/107; A61M 16/1095; A61M 16/12; A61M 16/14; A61M 16/16; A61M 16/161; A61M 16/20; A61M 16/202; A61M 16/204; A61M 16/205; A61M 16/207; A61M 16/208; A61M 16/209; A61M 2016/0018; A61M 2016/0021; A61M 2016/0027; A61M 2016/0033; A61M 2016/0036; A61M 2016/0039; A61M 2202/0007; A61M 2202/0208; A61M 2202/03; A61M 2205/15; A61M 2205/16; A61M 2205/18; A61M 2205/33; A61M 2205/3334; A61M 2205/3368; A61M 2205/3375; A61M 2205/3561; A61M 2205/3592; A61M 2205/502; A61M 2205/581; A61M 2205/582; A61M 2205/7518; A61M 2205/8206; A61M 2205/8237
See application file for complete search history.

(56) References Cited

U.S. PATENT DOCUMENTS

| | | | |
|---|---|---|---|
| 5,237,987 A * | 8/1993 | Anderson | A61M 16/202 128/204.21 |
| 6,237,594 B1 * | 5/2001 | Davenport | A61M 16/0677 128/204.26 |
| 8,944,057 B2 | 2/2015 | Hill et al. | |
| 10,617,840 B2 * | 4/2020 | MacLoughlin | A61M 16/1095 |
| 2005/0076906 A1 * | 4/2005 | Johnson | A61M 16/0051 128/204.21 |
| 2005/0284469 A1 | 12/2005 | Tobia et al. | |
| 2008/0017198 A1 | 1/2008 | Ivri | |
| 2008/0210242 A1 * | 9/2008 | Burk | A61M 16/06 128/206.21 |
| 2009/0241948 A1 | 10/2009 | Clancy et al. | |
| 2010/0258114 A1 | 10/2010 | Cortez, Jr. et al. | |
| 2011/0253136 A1 * | 10/2011 | Sweeney | A61M 16/161 128/207.18 |
| 2014/0290646 A1 | 10/2014 | Koehler et al. | |
| 2017/0182266 A1 | 6/2017 | Power | |

FOREIGN PATENT DOCUMENTS

| | | |
|---|---|---|
| WO | WO 2005/048982 | 6/2005 |
| WO | WO 2011/057235 A2 | 5/2011 |
| WO | WO 2012/079684 A1 | 6/2012 |
| WO | WO 2013/163527 A1 | 10/2013 |

* cited by examiner

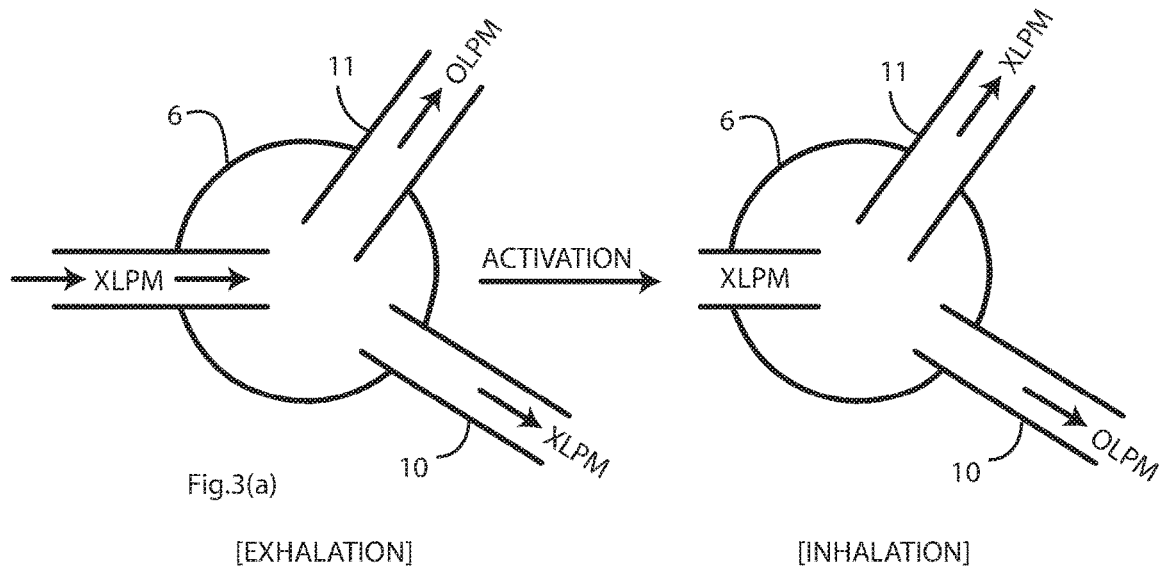
Fig.3(a)  [EXHALATION]   [INHALATION]
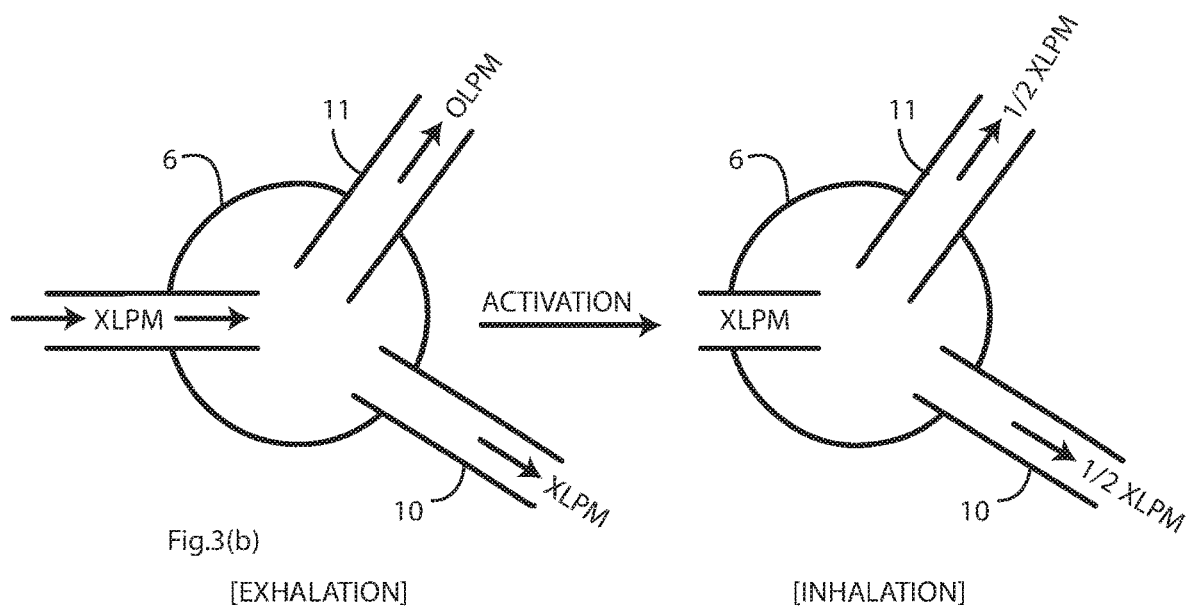
Fig.3(b)  [EXHALATION]   [INHALATION]

HIGH FLOW NASAL THERAPY SYSTEM

CROSS-REFERENCE TO RELATED APPLICATIONS

This application is a continuation of U.S. application Ser. No. 15/301,318, filed Sep. 30, 2016, which is the U.S. national phase entry under 35 U.S.C. § 371 of International Application No. PCT/EP2015/057866, filed on Apr. 10, 2015, which claims priority to European Patent Application No. 14164468.2, filed on Apr. 11, 2014. The contents of each of these are incorporated herein by reference in their entirety.

INTRODUCTION

The invention relates to delivery of aerosol to the respiratory tract via the nasopharynx "high flow nasal therapy" ("HFNT").

Currently, aerosol can be delivered during HFNT using a vibrating mesh nebuliser (or other aerosol generator) and a T-piece positioned in the flow path.

US2008/0017198 (Ivri) describes an aerosol delivery apparatus for pressure-assisted breathing systems.

WO2013/163527 (Medstar Health) describes an aerosol system with an inspiratory limb and an expiratory limb.

US2005/0284469 (Tobia et al) describes a system with a nebulizer and a gas monitoring device downstream of the nebulizer.

WO2012/079684/US2014/0290646 (NLI GmbH) describes a nasal inhalation device with a controller for applying a pattern to activation of an aerosol generator. This relies on exhalation down a separate dedicated limb whilst aerosol is being generated in the inspiratory limb.

WO2005/048982 (Nektar) describes a ventilator circuit with aerosol delivery, in which there is an inhalation line and an exhalation line.

FR2783431 (System Assistance Medical) describes a nebulizer with main and secondary ducts.

A major problem with HFNT is that often only small quantities of aerosol are delivered to the patient's respiratory tract, due to losses during patient exhalation or droplet impaction in the high flows required for HFNT.

Also, where a jet nebulizer is used for HFNT, it requires 6 to 8 l/min to generate aerosol. This requires that an additional flow be added to the flow being delivered to the patient, and this additional flow must be accounted for. This is problematic during the delivery of HFNT therapy to paediatrics and neonates who can require flows in the range 1 to 3 l/min. The flow required to drive the jet nebuliser would exceed this flow.

Also, both jet and ultrasonic nebulizers have high residual volumes. Moreover, ultrasonic systems can overheat the medication thereby potentially inactivating/denaturing labile formulations.

The invention addresses these problems.

SUMMARY OF THE INVENTION

According to the invention, there is provided high flow nasal therapy system comprising:
a gas supply,
a humidifier,
a nebulizer,
a flow line,
a nasal interface or a coupler for connection to an external interface, and
a controller configured to control the system in real time to vary the aerosol delivery to the nasal interface on a temporal basis,
wherein the controller is configured to provide an increased aerosol delivery during patient inhalation and reduced aerosol delivery during patient exhalation.

In one embodiment, the system comprises at least two branches and a valve linked with the controller, the branches including a first branch for delivery of aerosol and a second branch for delivery of non-aerosolized gas, and the controller is configured to control delivery into the branches, in which flow is unidirectional in the first and second branches, from the gas supply towards the nasal interface.

In one embodiment, the first branch includes the nebulizer. In one embodiment, the first branch includes a line configured to store a bolus of aerosol during flow through the second branch.

In one embodiment, the valve comprises a Y-junction between the gas inlet on one side and the branches on the other side. In one embodiment, the valve is configured to perform splitting of inlet gas flow between the branches with a desired proportional split set according to the controller. In one embodiment, the first branch has a larger cross-sectional area than the second branch.

In one embodiment, the controller is configured to reduce inlet gas flow during at least some of the time that flow is directed through the first branch. In one embodiment, one or both of the branches comprises a heater.

In one embodiment, the first and second branches join at their patient ends at a common conduit, and said common conduit is in turn linked with said nasal interface or coupler.

In one embodiment, the humidifier is included in the second branch. Preferably, the first branch comprises a heater, and the controller is configured to control said heater to provide the first branch with an elevated temperature compared to the second branch.

In one embodiment, the cannula comprises prongs each of which is linked with a dedicated one of the first and second branches. In one embodiment, the first branch includes a restrictor for causing more restricted flow through said first branch than through the second branch.

In one embodiment, the controller is configured to control aerosol delivery at least partly according to a configured control scheme. In one embodiment, the configured control scheme is set according to dosage requirements. Preferably, the controller is configured to control aerosol delivery according to detection of periods of altered activity such as sleep.

In one embodiment, the controller is configured to control aerosol delivery to remove any rainout building up in a breathing circuit by means of temporally varying aerosol output. In one embodiment, the controller is configured to control aerosol delivery on the basis that controlling pressure or flows may help avoid wastage of medication.

In one embodiment, the controller is configured to control the gas flow generator to reduce the gas flow rate to optimal levels for the duration of aerosol therapy only, and to restore gas flow rates again at end of dose.

In one embodiment, the controller is configured to control gas flow according to detection of end of dose.

In one embodiment, the controller is configured to control aerosol delivery for protection of equipment. In one embodiment, the system comprises a sensor for detecting flow conditions and the controller is adapted to vary the aerosol output at least partly in response to sensed flow conditions. In one embodiment, the sensor comprises a flow meter. In one embodiment, the sensor includes a pressure transducer. In one embodiment, the sensor is downstream of the nebulizer.

In another aspect, the invention provides a method of operating, by a controller, a high flow nasal therapy system comprising a gas supply for providing an inlet gas flow, a humidifier, a nebulizer, a flow line, a nasal interface or a coupler for connection to an external interface, the method comprising the controller varying aerosol delivery to the nasal interface on a temporal basis.

In one embodiment, the method comprises the step of the controller providing an increased aerosol delivery during patient inhalation and reduced aerosol delivery during patient exhalation.

In one embodiment, the method comprises the steps of:
providing in the system a sensor to sense patient inhalation and exhalation,
providing in the system, as said flow line, at least a first branch and a second branch,
delivering an inlet gas into the branches, in which:
the inlet gas flow is divided between the branches to provide increased aerosol delivery to the nasal interface during sensed inhalation and reduced aerosol delivery during sensed exhalation.

In one embodiment, the method comprises the steps of:
delivering the inlet gas into the branches so that flow is unidirectional in the first and second branches, from the gas supply towards the nasal interface, in a manner to provide positive ventilator support during both patient inhalation and exhalation,
delivering aerosol in the first branch, and
delivering non-aerosolized gas in the second branch.

In one embodiment, the method comprises the step of generating the aerosol in the first branch.

In one embodiment, the method comprises the step of storing a bolus of aerosol in the first branch during flow through the second branch.

In one embodiment, the method comprises the step of reducing inlet gas flow during at least some of the time that flow is directed through the first branch.

In one embodiment, the method comprises the step of heating one or both of the branches.

In one embodiment, the method comprises the step of humidifying gas in the second branch using a humidifier located in said second branch. In one embodiment, the method comprises the step of heating gas in the first branch to provide the first branch with an elevated temperature relative to gas in the second branch. In one embodiment, the method comprises the step of restricting gas flow through said first branch relative to gas flow through the second branch.

In one embodiment, the method comprises the step of the controller controlling aerosol delivery at least partly according to a control scheme with dosage requirements. In one embodiment, the method comprises the steps of detecting patient activity and controlling aerosol delivery according to detected periods of altered activity. In one embodiment, the method comprises said detected activity is sleep.

In one embodiment, the method comprises the step of the controller controlling a gas flow generator to reduce the inlet gas flow rate during aerosol therapy only, and restoring the inlet gas flow rate at end of dose.

According to the invention, there is provided a high flow nasal therapy system comprising a gas supply, a nebulizer, a flow line, a nasal interface or a coupler for connection to an external interface, and a controller, wherein the controller is adapted to control the system to vary the aerosol output on a temporal basis.

In one embodiment, the controller is adapted to perform said control in real time. In one embodiment, the controller is adapted to provide an increased aerosol delivery during patient inhalation and reduced aerosol delivery during patient exhalation. Preferably, the system comprises a sensor for detecting flow conditions and the controller is adapted to vary the aerosol output at least partly in response to sensed flow conditions.

In one embodiment, the sensor comprises a flow meter. In one embodiment, the sensor includes a pressure transducer. In one embodiment, the sensor is downstream of the nebulizer.

In another embodiment, the controller is adapted to control one or more operating parameters of the nebulizer to vary the output.

In one embodiment, the controller is adapted to vary gas flow rate to vary aerosol output.

In one embodiment, the system comprises at least two branches and a valve linked with the controller, the branches including a first branch for delivery of aerosol and a second branch for delivery of non-aerosolized gas, and the controller is adapted to control delivery form the branches.

In one embodiment, the first branch includes the nebulizer. Preferably, the first branch includes a line adapted to store a bolus of aerosol for release under control of the controller. In one embodiment, the valve provides a Y-junction between the gas inlet on one side and the branches on the other side.

In one embodiment, the controller is adapted to control aerosol delivery at least partly according to a configured control scheme. In one embodiment, the configured control scheme is set according to dosage requirements.

In one embodiment, the controller is adapted to control aerosol delivery according to detection of periods of non-activity such as sleep. Preferably, the controller is adapted to control aerosol delivery to remove any rainout building up in a breathing circuit.

In one embodiment, the controller is adapted to control aerosol delivery on the basis of inspiratory pressure or flows may help avoid wastage of medication.

In one embodiment, the controller is adapted to control aerosol delivery to reduce the gas flow rate to optimal levels for the duration of aerosol therapy only, and to restore gas flow rates again at the end of dose. In one embodiment, the controller is adapted to control aerosol delivery according to detection of end of dose. In one embodiment, the controller is adapted to control aerosol delivery for protection of equipment.

DETAILED DESCRIPTION OF THE INVENTION

The invention will be more clearly understood from the following description of some embodiments thereof, given by way of example only with reference to the accompanying drawings in which: —

Figure 2A:
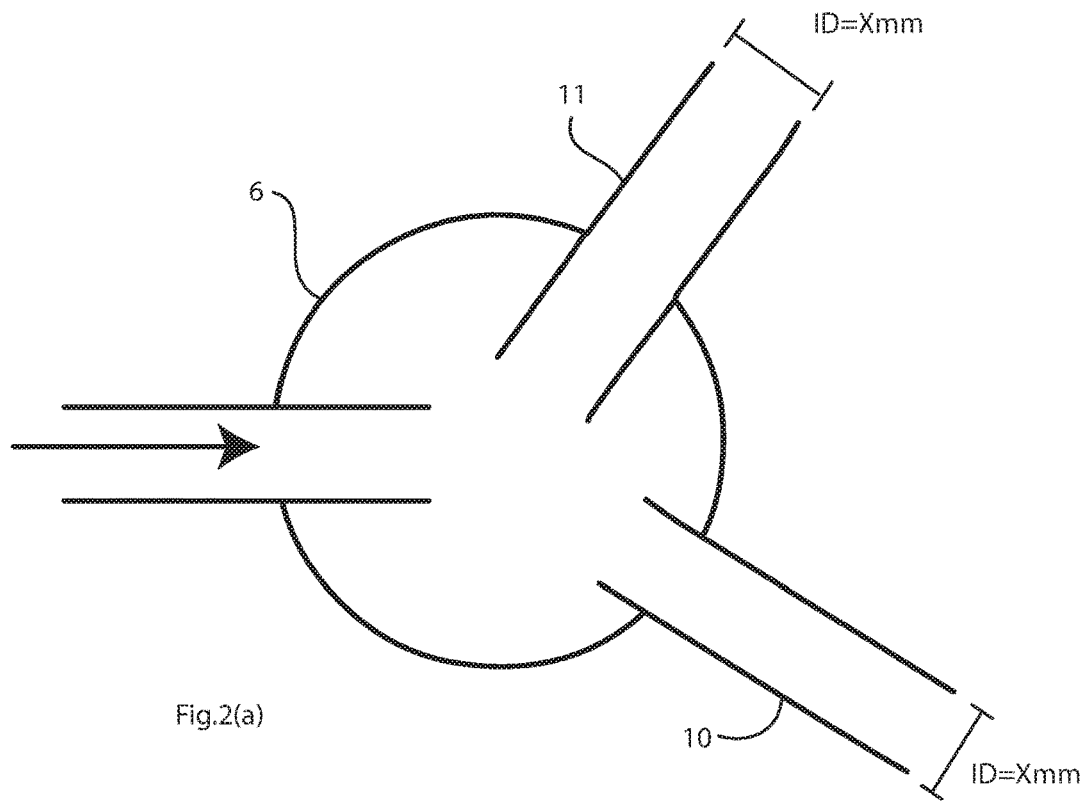
Figure 2B:
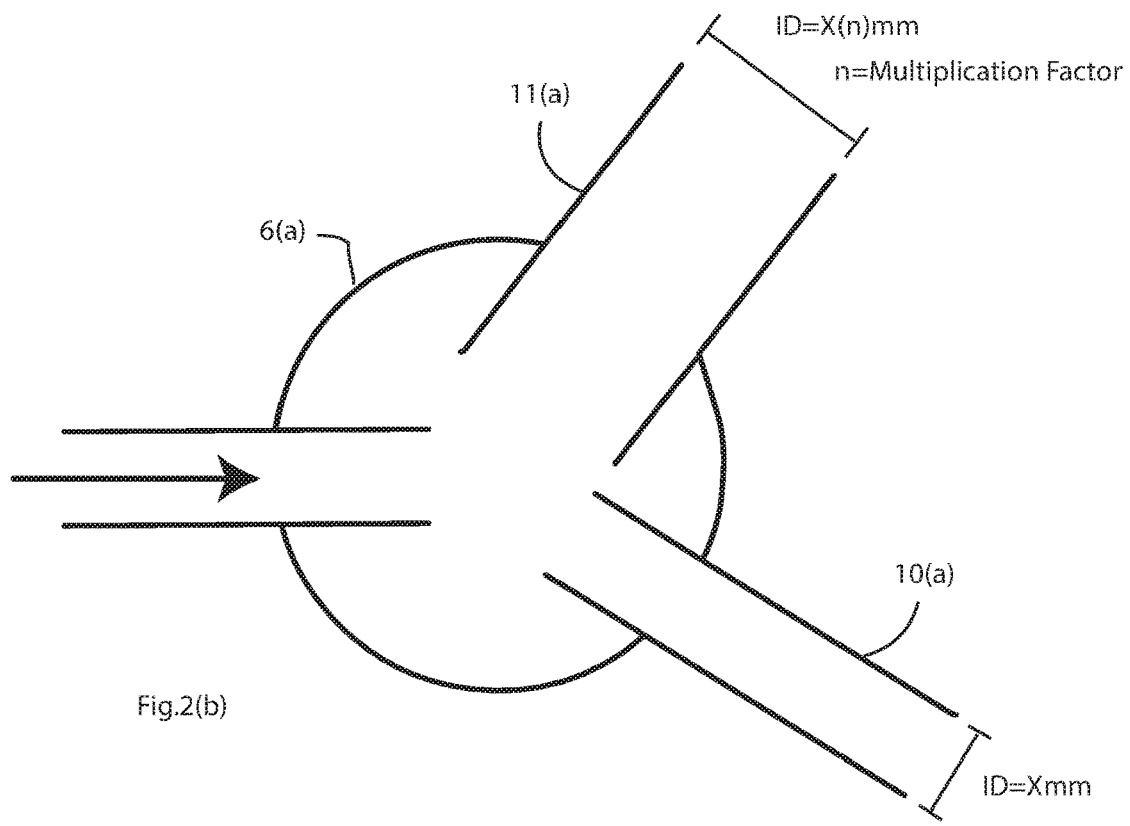
Figure 4:
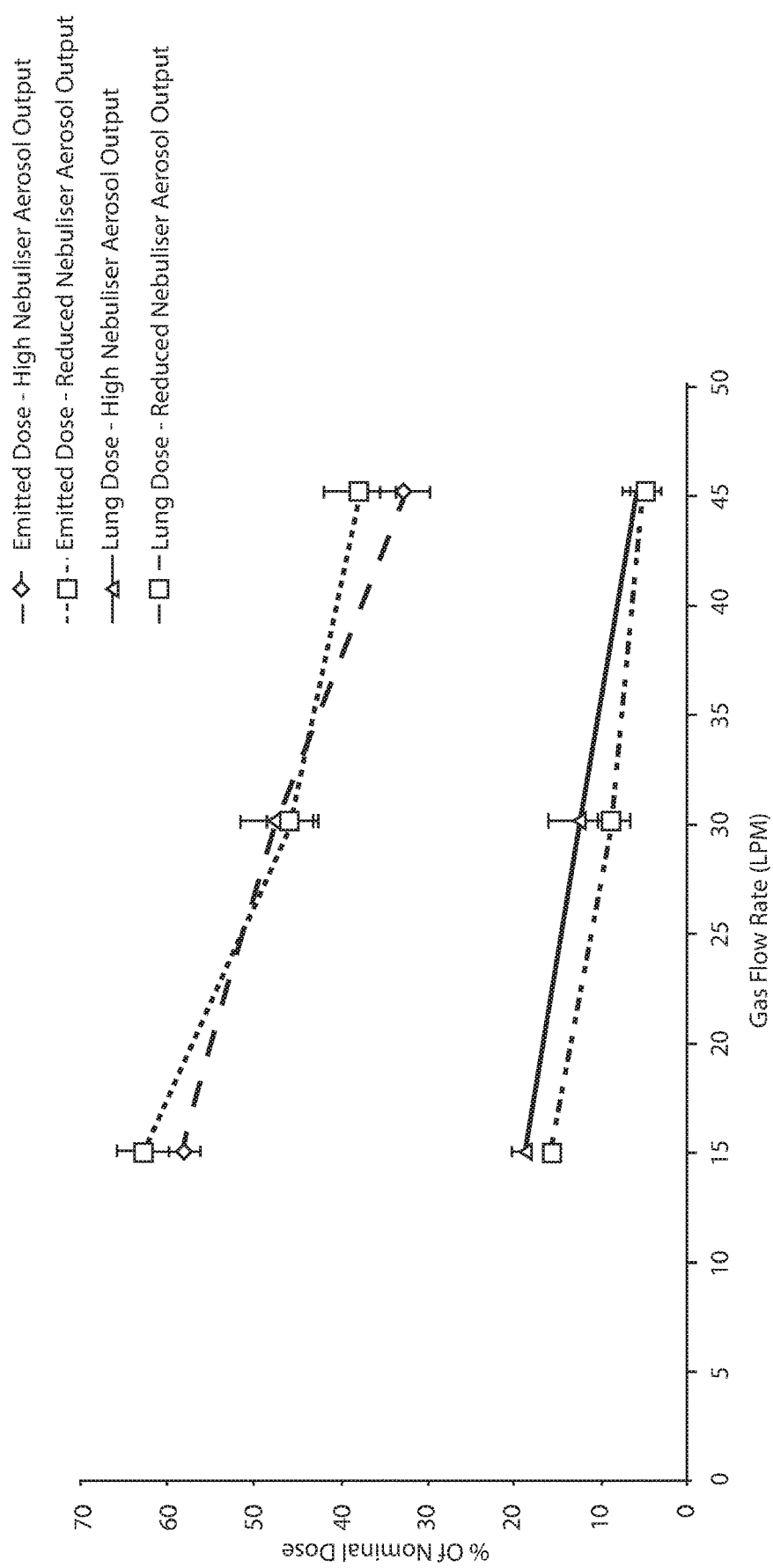
Figure 5A:
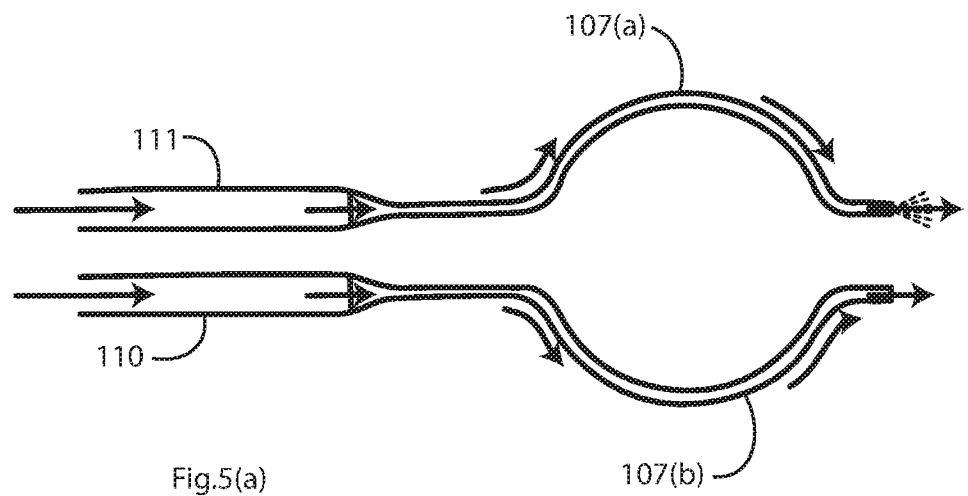
Figure 5B:
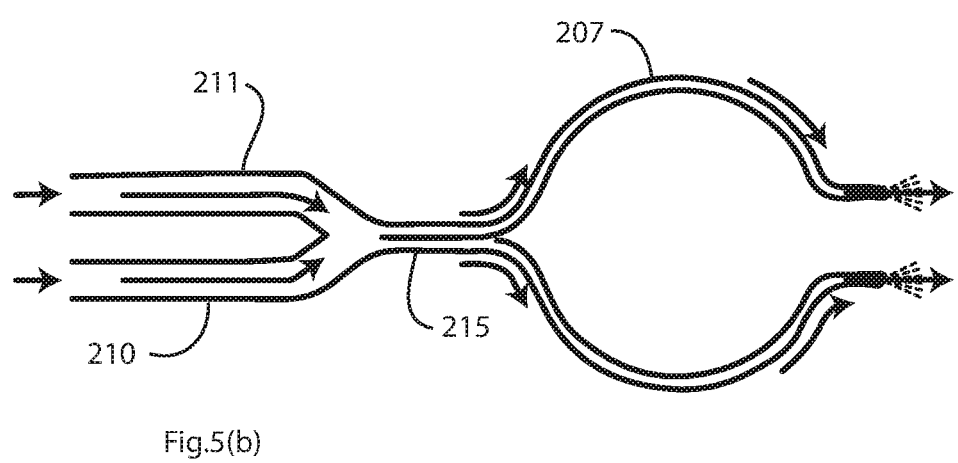
Figure 6:
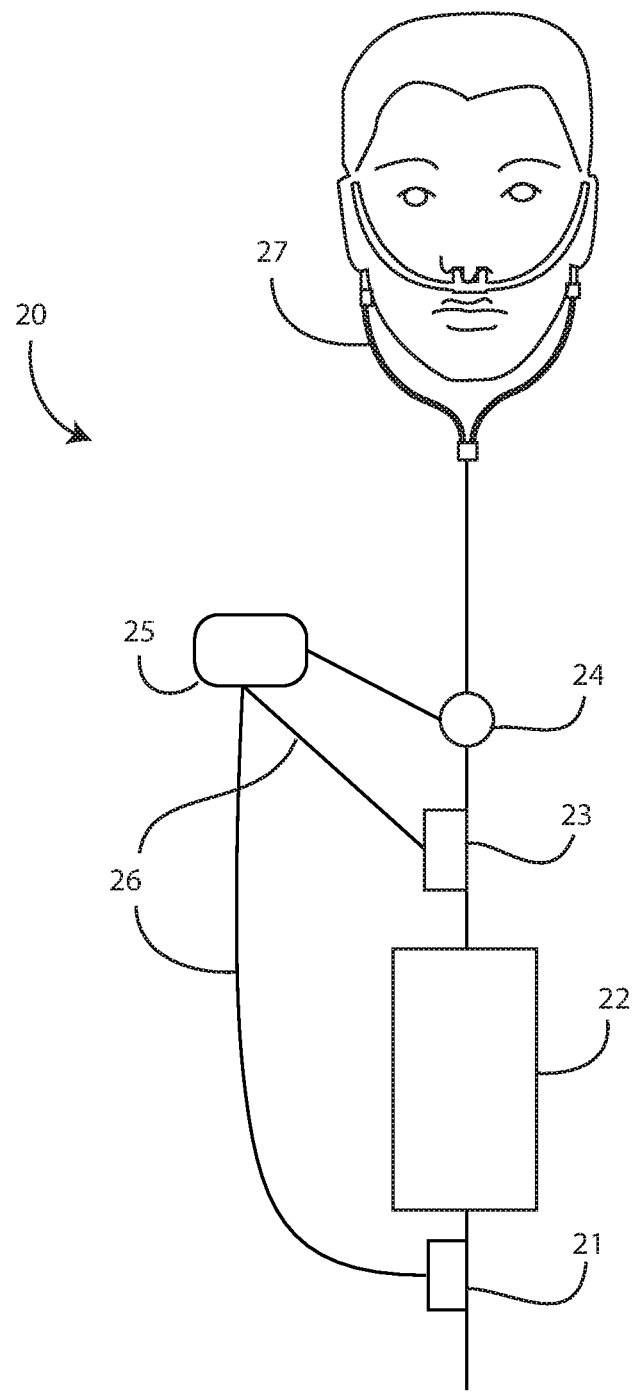

FIG. 1 is a diagram illustrating a HFNT system of the invention;

FIGS. 2(a) and 2(b) are diagrams showing different arrangements of limb size extending from the valve which controls flow into and between the limbs, FIGS. 3(a) and 3(b) illustrate different control schemes with continuous variation between the limbs, FIG. 4 is a set of plots showing emitted dose and respirable dose efficiencies recorded across actively controlled gas flow rates, FIGS. 5(a) and 5(b) are diagrams showing different arrangements for connection of the limbs to a cannula, in which each limb feeds a single cannula prong only, and FIG. 6 is a diagram illustrating an alternative system.

Referring to FIG. 1 a system 1 comprises a gas inlet 2 feeding a regulator 3, in turn feeding a needle valve 4. This feeds a humidifier 5 which actively humidifies the gas and feeds the humidified gas to a flow splitter valve 6. The latter is in this embodiment an electronic 3-way valve from which there are two branches (or "limbs") leading to a nasal interface (e.g. cannula, mask, pillow) 7. Control is provided by an electronic controller 16.

The branches are a first branch 10 which is primarily for receiving humidified air only (that is to say never exposed to aerosolised medicament), and a second branch 11 having a nebulizer chamber 12 and a line 13 for delivery of aerosol carried in the humidified gas. There is also a sensor to detect patient inhalation and exhalation, in this case a flow meter 15 across the limbs at the patient end. The function of the flow meter 15 is to detect when the patient is inhaling, and thereafter provide a signal for control of the electronic 3-way valve 6.

The feedback signal from the sensor 15 is only used to change the limb through which the airflow is delivered. The positive pressure gas flow is unidirectional and it is not intended, or likely, that the patient exhales back down one or both limbs at any time throughout the breathing cycle. Splitting the unidirectional flow path into two limbs allows for aerosol bolus accumulation in the limb 11 whilst the patient is exhaling. The advantage of aerosol bolus delivery derives from the inhalation of high concentration aerosol medicament with minimal medicament wastage during exhalation as is a problem with some prior art approaches.

The bolus will build up in the limb 11 due to the lack of flow through this limb during periods of the breath cycle not associated with inhalation. The only activity generated in the limb 11 during these periods will be by the aerosol generator releasing aerosol droplets into the limb. This limb 11 is not sealed proximal to the patient and in the case of extended periods excess build-up of aerosol may exit limb 11 at the terminal of the line 13. All aerosol droplets released into the limb 11 are potentially available to the patient when required. The controller 16 and the valve 6 actively switch limbs as a means of aerosol protection.

The apparatus 1 achieves an advantageous means of aerosol protection whilst maintaining positive pressure ventilator support during exhalation continuously at all times. In contrast, in the prior approach of having a dedicated inhalation limb and a dedicated exhalation limb to take the exhalation flow in the opposite direction, there may be either 1) positive pressure support during exhalation by having the inspiratory limb with a gas flow (preventing the accumulation of an aerosol bolus), or 2) it does not provide positive pressure ventilatory support during exhalation.

Advantageously, in the invention described herein there is continuous provision of ventilatory support.

The gas flow rate in the first branch 11 can be relatively reduced by means of a flow restrictor. This may for example be a narrower section of tubing, an array of holes in a plate, or by means of the degree to which the flow splitter 6 opens, allowing for a controlled gas flow to pass through. A gas flow rate, for the branch 11 which is lower than that passing through the second branch 10 allows for maximal entrainment of suspended aerosol droplets whilst mitigating the risk of aerosol losses through inertial impaction in high flows.

One or both of the limbs 10 and 11 may in some embodiments be heated by means of a heater such as a heated wire in the lumen of the limb or alternatively arranged around the circumference of the limb. Heated tubing is not a requirement but is desirable. The inner diameters of the limbs 10 and 11 can be equal. However it is envisaged that the limb 11 may have a larger inner diameter than that of the limb 10. This arrangement would i) increase the internal volume of the limb such that a larger bolus of aerosol can be stored, ii) reduce gravitational/sedimentary and inertial aerosol losses within limb 11 during the aerosol bolus-building periods where the gas flow is exclusively passing through the limb 10, and iii) to reduce the velocity of the gas passing through the limb 11 thereby reducing the potential for inertial aerosol losses.

Of note, for all combinations of gas flow and limb usage, positive pressure ventilatory support is provided to the patient at all times, i.e. during inhalation, positive pressure ventilatory support is provided via limb 11, during exhalation, positive pressure ventilatory support is provided via limb 10.

FIG. 2(a) illustrates the embodiment where the limbs 11 and 10 are of equal dimensions, whereas FIG. 2(b) illustrates an embodiment in which where the aerosol limb (11(a)) is wider.

Further, the limb 11 may be extended in length when compared with the limb 10. Also, the line 13 may in some embodiments be expandable, but this is not essential. In this embodiment the line 13 is the post-nebuliser side of branch 11 suitable to be filled with aerosol.

The system 1 delivers aerosol therapy during HFNT. It cyclically accumulates a bolus of aerosol in the line 13, of the branch 11.

The cycle in this embodiment is the breathing cycle and the bolus is accumulated in the line 13 during exhalation. The flow to the patient reverts to non-aerosol laden humidified air in the branch 10 during exhalation. Switching is achieved by means of the electronically controlled 3-way valve 6. At all times the flows in the branches are towards the patient in both of the limbs 11 and 10. The patient's exhaled gas exits the patient via the mouth and to the air, and around the cannula in the nose to the air. Exhaled gas does not flow down the branches 11 or 10 as they are pressurised.

The positive pressure gas flow is unidirectional and it is not intended, or likely, that the patient exhales back down one or both limbs at any time throughout the breathing cycle. Splitting the unidirectional flow path into two limbs is particularly effective at allowing aerosol bolus accumulation in the limb 11 whilst the patient is exhaling. This helps to achieve the inhalation of high concentration aerosol medicament with minimal medicament wastage during exhalation as is the problem in the prior art.

The feedback for the valve 6 control may take the form of a pressure change (positive or negative, measured with a pressure transducer), flow rate change (measured with a flow meter), respiratory gas (e.g. $CO_2$ measured with an appropriate monitor capable of real time digital outputs). Feedback may also take the form of manual user inputs such as button presses. The controller may have an "aerosol delivery mode" on a software GUI or other user interface. On selection of this mode, the valve 6 may act according to its preprogramed instructions to regulate gas flow between the limbs 10 and 11. Under conditions where the aerosol delivery mode is not selected, the valve 6 can act to split the gas flow through one or both of the limbs 10 and 11 concurrently.

Because the controller prevents gas flow in the branch 11 during patient exhalation, it allows for the accumulation of aerosol as a bolus as it is not cleared from the branch. Accumulation of aerosol as a bolus results in a high concentration of aerosol being available immediately on inhalation, and thereby improves efficiency of aerosol delivery to the patient.

In alternative embodiments the switching may be according to a different control scheme. For example, where perhaps a drug may only be suitable for delivery once every half hour, the controller may operate the valve 6 so that the flow is from the branch 11 at this frequency. The system provides the flexibility of delivering aerosol either breath-by-breath or for pre-defined portions of treatment. The control scheme may be factory-set or it may in alternative embodiments be configurable by the clinician or by the user.

In all cases, the controlled division between the branches avoids need to dynamically control the output of the nebulizer 12, although this may additionally be done. The valve 6 is controlled so that the inlet flow is directed in varying proportions between 0% and 100% between the branches 11 and 10.

In more detail, upon receipt of the feedback signal;
a) The 3-way valve switches to limb 11 only, resulting in no gas flow entering the limb 10 (0 litres per minute (LPM)) and all gas flow entering limb 11 (X LPM).
b) The 3-way valve splits the gas flow between limbs 10 and 11. The split may take the form of (% of gas flow: % of gas flow) 50:50, 90:10, 25:75 as examples.

These control schemes are illustrated in FIGS. 3(*a*) and 3(*b*).

Under these gas flow conditions, the aerosol generator may be activated or not, depending on the user selected options.

The internal geometries of the line 13 may be different from those of the line 10 so as to allow for maximal generation and storage of the aerosol bolus. These differences may include any or all of the following, but are not limited to; the use of smooth tubing as opposed to corrugated tubing, larger internal diameter tubing, longer length tubing. Additionally, the internal geometries of the line 13 may be different from those of line 10 so as to allow for alteration of the aerosol carrier gas velocity.

The valve 6 may be controlled according to the needle valve/flow regulator 6 such that when the gas flow is being directed down the limb 11, or a combination of limbs 10 and 11, the total gas flow is reduced by the gas flow controller 4. This embodiment is designed to reduce aerosol losses within the limb 11 in an effort to increase the emitted fraction of aerosol. The benefits are illustrated in the plots of FIG. 4.

Referring to FIG. 5(*a*), in another embodiment an aerosolisation limb 111 similar to the limb 11 and a gas-only limb 110 similar to the limb 10 feed a nasal cannula 107 with two separate prongs 107(*a*) and 107(*b*) each for a single nare. In operation, it is likely that gas flow would be delivered down both limbs 110 and 111 such that the back pressure generated by such a restriction would not interfere with gas flow being delivered to the patient. A potential advantage is that given aerosol shall enter the nasopharynx via one nostril only there will be no mixing of aerosol streams, thereby increasing aerosol rainout in the naso and oropharynx. Another potential advantage is the alternating of pressure build-up between nostrils. It is believed by some that mononasal HFNT reduces intercranial pressure.

In another embodiment, as shown in FIG. 5(*b*) a limb 210 and a limb 211 join at a conduit 215 prior to connection with a cannula 207.

It will be appreciated that the system optimises gas flow rates and aerosol delivery efficiency for HFNT. Positive end expiratory pressures can be controlled by the caregiver. The system can provide feedback to the user regarding flow rates and pressures to achieve optimum therapy.

Table 1 lists examples of the logic flows used in this system.

TABLE 1

| Logic flow | |
| --- | --- |
| INPUT to system | OUTPUT from system |
| User inhalation detected by pressure transducer | 3-way valve switches to allow flow to pass through aerosol limb 11 only |
| User exhalation detected by pressure transducer | 3-way valve switches to allow flow to pass through limb 10 only |

Referring To FIG. 6 an alternative system 20, comprises:
21=Air inlet
22=Humidifier
23=Nebulizer
24=Flow Meter in line to patient interface
25=Nebulizer power supply and output controller
26=Communication lines between 25 and 21 or 23
27=Patient interface, e.g. nasal cannula The gas inlet 21 has a regulator feeding a needle valve Z. This feeds the humidifier 22 which actively humidifies the gas and feeds the humidified gas to the patient circuit. The patient circuit leads to the nasal interface 27 (for example cannula, mask, and/or pillow). The system control unit 25 houses a standalone flow generator, including but not limited to a fan.

The gas flow rate within the system can be detected by means of the flow meter 24 or alternatively by an electronic or mechanical signal supplied by the regulator, in the case of an integrated device providing both user interface and flow generation and regulation. These components are connected directly with and supply a signal to the nebuliser controller 25.

The nebuliser controller 25 controls nebuliser output described as aerosol flow rate (millilitres of medicament aerosolised per minute), aerosol density (number of aerosol droplets per unit volume of gas) or intermittent on-off pulses, of varying durations, of aerosol generation.

The nebuliser 23 may be placed on the gas inlet side of the humidifier 22 or the patient side of the humidifier 22, and its operation is directly controlled by the nebuliser controller 25. Placement of the nebuliser 23 on the gas inlet side of the humidifier 22 allows for pre-conditioning of the gas prior to humidification. The nebuliser shall ideally emit a droplet size in the range of 0.1 to 10 microns MMAD, however droplets up to 20 microns MMAD may find utility in targeting the nasal passages specifically.

Communication between the gas flow generator control unit and/or the flow meter 24 will identify no gas flow conditions that will be converted to a signal sent to the nebuliser controller 25 and/or the humidifier 22. In this instance of no-flow, or backward flow (flow coming from the patient side towards the flow generator) the nebuliser 23 and/or the humidifier 22 shall be prevented from generating aerosol and/or humidity. The function of this feature is to protect internal electronics, fans and other components of the flow generator and control unit from exposure to aerosol or humidity.

The detection of gas flow rate may result in one of several conditions including, but not limited to; control of the nebuliser output or control of the gas flow rate on a temporary basis.

In the instance where the nebuliser output is controlled, predefined output settings shall be supplied by the controller 25 to the nebuliser 23. These output settings may include, but are not limited to: reduction of aerosol output concurrent with high gas flow rates, or alternatively an increase in nebuliser output concurrent with low gas flow rates. The function of this control is to optimise aerosol delivery to the patient.

In the instance where gas flow rate is controlled, gas flow rates may be reduced or increased on a temporary basis in order to allow for optimised aerosol delivery to the patient.

In the system 20 gas flow rate can be monitored in the following ways:

Integrated control of/from electromechanical gas flow generator, for example standalone fan capable of generating therapeutically relevant gas flow rates in the range of 0 to 100 litres per minute.

Pressure transducer, which is in fluid communication with gas flow limb, incorporated into nebuliser controller system.

Digital Flow meter, which is in fluid communication with gas flow limb, incorporated into nebuliser controller system.

Referring again to FIG. 4, this shows plots for emitted dose and respirable dose delivery rates across gas flow rates for both high and reduced nebuliser outputs following dynamic nebuliser aerosol output monitoring and control. It will be seen that the slopes are similar, both being downward indicating lower dose with increased gas flow.

The data for the plots of FIG. 4 is given in Table 2 below.

TABLE 2

Emitted dose and tracheal dose (expressed as a percentage of the nominal dose placed in the nebuliser prior to test) across 3 standard gas flow rates for both high and reduced aerosol output.

|  | Emitted dose (%)[1] | | Tracheal Dose (%)[2] | |
| --- | --- | --- | --- | --- |
| Gas Flow Rate (Litres per minute) | High Aerosol Output | Reduced Aerosol Output | High Aerosol Output | Reduced Aerosol Output |
| 15 | 58.05 ± 1.95 | 62.73 ± 3.05 | 18.95 ± 1.32 | 15.75 ± 0.47 |
| 30 | 47.17 ± 4.45 | 45.96 ± 2.68 | 12.44 ± 3.72 | 8.50 ± 1.79 |
| 45 | 32.59 ± 2.89 | 37.86 ± 4.19 | 5.81 ± 1.40 | 4.87 ± 1.66 |

NOTES:
[1]Emitted dose describes the percentage of the nominal nebuliser dose exiting the system with no simulated patient breathing.
[2]Tracheal dose describes the percentage of the nominal nebuliser dose delivered beyond the trachea in a model of a simulated breathing adult patient.

Table 3 below lists examples of the logic flows used in this system.

TABLE 3

| INPUT to system | OUTPUT from system |
| --- | --- |
| Control unit programmed by user to a set flow rate | Nebuliser output altered |
| Control unit programmed by user to a set flow rate | Pre-programed software does not allow selected gas flow rate to be generated during aerosol therapy User informed of suboptimal aerosol delivery conditions |
| Control unit programmed by user to a set nebuliser aerosol output | Nebuliser aerosol output increased. Nebuliser aerosol output decreased for optimal aerosol delivery conditions in high gas flow Nebuliser aerosol output decreased for extended e.g. all day or overnight delivery of medication |
| Flowmeter detects no gas flow | No aerosol generated |

Aerosol output can be controlled by real-time software monitoring of gas flow rates, and subsequent control of nebuliser power or cycling.

Real-time monitoring of gas flow and concurrent adjustment of aerosol output to pre-set levels has applications across several patient interfaces.

One primary use may be the day-long, long-term use of high flow nasal therapy (HFNT). Patients receiving HFNT often wear the device 24-hours a day and during periods of non-activity (e.g. sleep) may increase or decrease the gas flow rate to comfortable levels. During this period, the patient may need to wake up in order to add more medication to the medication cup, or alternatively remove any rainout building up in their breathing circuit.

Other examples of single limb, positive pressure-only systems include non-invasive ventilation systems, e.g. CPAP and BiPAP. Control of nebuliser output on the basis of inspiratory pressure or flows may help avoid wastage of medication.

In instances where the nebuliser system is integrated into a standalone gas flow generator or regulator for short term use, and where therapeutically acceptable, the control mechanism may be used to reduce the gas flow rate to optimal levels for the duration of aerosol therapy only, and restoring gas flow rates again at the end of dose.

Protection of equipment. On occasions where the nebuliser control system is integrated into a standalone gas flow generator or regulator, the optimal placement of the nebuliser for respirable dose optimisation may result in aerosol being generated close to electronics or components that could be adversely affected by aerosol, e.g. float valves on humidifier chambers. Detection of a "no-flow" or "low-flow" condition could be used to prevent generation of aerosol, and thereby protect the incumbent equipment.

The invention is not limited to the embodiments described but may be varied in construction and detail. For example the humidifier may be located in the non-aerosolisation branch only. Where the humidifier is in a common inlet, then it may be controlled to have a reduced or zero output when the flow is only through the aerosolized branch. Humidity is known to alter (increase) droplet size and so under the conditions described where airflow is directed through the limb 11 the risks of increased aerosol losses in humidified air are mitigated.

Also, it is envisaged that the system may include a means of control of aerosol output to a level deemed appropriate for the gas flow rate being delivered (not on the basis of patient-side sensor feedback. In this embodiment, control of aerosol output is in fluid or digital communication with the gas flow generator. At various gas flow rates aerosol output can be varied in order to maximise the emitted aerosol dose from the system. Variations in aerosol output can take the form of on/off, or reduced/increased output. Further, on selection of an "aerosol delivery mode" the system may act to temporarily reduce the gas flow rate for the duration of active aerosol generation. FIG. 4 illustrates the effect of varying both aerosol output and gas flow rate on emitted dose from the system. Under conditions where reduced gas flow rates are not appropriate (clinically) aerosol generator output can be varied to the same effect.

The invention claimed is:

1. A high flow nasal therapy system comprising:
a gas supply,
a humidifier,
a nebulizer,
a flow line having a first branch for delivery of aerosol and a second branch for delivery of non-aerosolized gas,
a nasal interface, and
a controller configured to control the system in real time to vary the aerosol delivery to the nasal interface on a temporal basis,
wherein the controller is configured to control delivery of inlet gas into the first branch and the second branch with a desired proportional split between the first branch and the second branch to provide aerosolized gas delivery during patient inhalation and delivery of non-aerosolized gas during patient exhalation.

2. The of high flow nasal therapy system claim 1, in which exhalant does not flow through the first branch or the second branch during exhalation.

3. The high flow nasal therapy system of claim 1, in which the humidifier is upstream of a split between the first branch and the second branch with respect to the gas supply.

4. A high flow nasal therapy system as claimed in claim 1, further comprising a valve linked with the controller, and the controller is configured to control delivery into the branches, in which flow is unidirectional in the first and second branches, from the gas supply towards the nasal interface.

5. A high flow nasal therapy system as claimed in claim 4, wherein the first branch includes the nebulizer.

6. A high flow nasal therapy system as claimed in claim 4, wherein the valve comprises a Y-junction between a gas inlet on one side and the branches on another side.

7. A high flow nasal therapy system as claimed in claim 4, wherein the valve is configured to perform splitting of the inlet gas flow between the branches with a desired proportional split set according to the controller.

8. A high flow nasal therapy system as claimed in claim 4, wherein the first branch has a smaller cross-sectional area than the second branch.

9. A high flow nasal therapy system as claimed in claim 4, wherein the controller is configured to reduce the inlet gas flow during at least some of the time that flow is directed through the first branch.

10. A high flow nasal therapy system as claimed in claim 4, wherein the first and second branches join at their patient ends at a common conduit, and said common conduit is in turn linked with said nasal interface.

11. A high flow nasal therapy system as claimed in claim 4, wherein the humidifier is included in the second branch.

12. A high flow nasal therapy system as claimed in claim 11, wherein the first branch comprises a heater, and the controller is configured to control said heater to provide the first branch with an elevated temperature compared to the second branch.

13. A high flow nasal therapy system as claimed in claim 11, wherein the first branch includes a restrictor for causing more restricted flow through said first branch than through the second branch.

14. A method of operating, by a controller, a high flow nasal therapy system comprising a gas supply for providing an inlet gas flow, a humidifier, a nebulizer, a flow line having a first branch for delivery of aerosol and a second branch for delivery of non-aerosolized gas, and a nasal interface, the method comprising:
varying, by the controller, aerosol delivery to the nasal interface on a temporal basis;
controlling, by the controller, delivery of the inlet gas into the first branch and the second branch with a desired proportional split between the first branch and the second branch to provide an increased aerosol delivery during patient inhalation and delivery of non-aerosolized gas during patient exhalation.

15. A method as claimed in claim 14, wherein the high flow nasal therapy system further comprises a sensor for detecting flow conditions, and wherein the controlling, by the controller, the delivery of the inlet gas into the first branch and the second branch with a desired proportional split between the first branch and the second branch includes:
controlling, by the controller, the delivery of the inlet gas into the first branch and the second branch with a desired proportional split between the first branch and the second branch to provide increased aerosol delivery to the nasal interface during sensed inhalation and reduced aerosol delivery during sensed exhalation.

16. A method as claimed in claim 15, further comprising:
delivering, by the controller, the inlet gas into the branches so that flow is unidirectional in the first and second branches, from the gas supply towards the nasal interface, in a manner to provide positive ventilator support during both patient inhalation and exhalation,
delivering, by the controller, aerosol in the first branch, and
delivering, by the controller, non-aerosolized gas in the second branch.

17. A method as claimed in claim 15, further comprising generating, by the controller, the aerosol in the first branch.

18. A method as claimed in claim 15, further comprising storing a bolus of aerosol in the first branch during flow through the second branch.

19. A method as claimed in claim 15, further comprising reducing inlet gas flow during at least some of an amount of time that flow is directed through the first branch.

20. A high flow nasal therapy system comprising:
a gas supply,
a humidifier,
a nebulizer,
a flow line having a first branch for delivery of aerosolized gas and a second branch for delivery of non-aerosolized gas,
a sensor for detecting flow conditions, a nasal interface or a coupler for connection to an external interface, and a controller configured to:
control the system in real time to vary the aerosol delivery to the nasal interface on a temporal basis, and deliver an inlet gas flow from the gas supply into the first branch and the second branch, the inlet gas flow being divided between the first branch and the second branch to provide aerosolized gas delivery during sensed inhalation and non-aerosolized gas delivery during sensed exhalation, and wherein the humidifier is upstream of a split between the first branch and the second branch with respect to the gas supply.

* * * * *

UNITED STATES PATENT AND TRADEMARK OFFICE
CERTIFICATE OF CORRECTION

| | |
|---|---|
| PATENT NO. | : 11,833,310 B2 |
| APPLICATION NO. | : 16/750507 |
| DATED | : December 5, 2023 |
| INVENTOR(S) | : Ronan MacLoughlin and Niall Smith |

It is certified that error appears in the above-identified patent and that said Letters Patent is hereby corrected as shown below:

In the Claims

Column 11, Line 38, Claim 2, delete "The of high flow nasal therapy system claim" and insert --The high flow nasal therapy system of claim--.

Signed and Sealed this
Sixth Day of February, 2024

Katherine Kelly Vidal
*Director of the United States Patent and Trademark Office*